United States Patent
Streicher et al.

Patent Number: 6,143,906
Date of Patent: *Nov. 7, 2000

[54] ASCORBYL SORBATES

[75] Inventors: Harald Streicher, Ludwigshafen; Linda von dem Bussche-Hünnefeld, Lampertheim; Horst Westenfelder, Neustadt; Hans-Ulrich Wekel, Ellerstadt, all of Germany

[73] Assignee: BASF Aktiengesellschaft, Ludwigshafen, Germany

[*] Notice: This patent issued on a continued prosecution application filed under 37 CFR 1.53(d), and is subject to the twenty year patent term provisions of 35 U.S.C. 154(a)(2).

[21] Appl. No.: 09/178,428

[22] Filed: Oct. 26, 1998

[30] Foreign Application Priority Data

Nov. 14, 1997 [DE] Germany .......................... 197 50 528

[51] Int. Cl.$^7$ ...................... C07D 307/40; C07D 307/42
[52] U.S. Cl. ............................................. 549/315
[58] Field of Search ............................................. 549/315

[56] References Cited

FOREIGN PATENT DOCUMENTS 0 313 304  4/1989  European Pat. Off. .

OTHER PUBLICATIONS

D. Darr, et al., British Journal of Dermatology, vol. 127, pp. 247–253, "Topical Vitamin C Protects Porcine Skin From Ultraviolet Radiation–Induced Damage", 1992.

B.M. Tolbert, et al., Annals of the New York Academy of Sciences, vol. 258, pp. 48–69, "Chemistry and Metabolism of Ascorbic and Ascorbate Acid Sulfate", Sep. 30, 1975.

Primary Examiner—Ba K. Trinh
Attorney, Agent, or Firm—Oblon, Spivak, McClelland, Maier & Neustadt, P.C.

[57] ABSTRACT

Ascorbyl sorbates of the formula I,

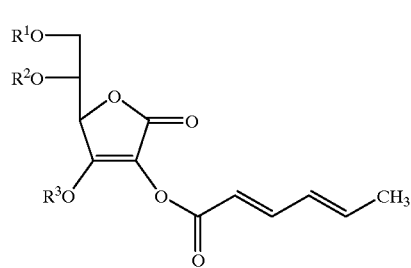

where the variables independently of one another have the following meanings:

$R^1$ and $R^2$
are hydrogen, $C_1$–$C_{12}$-alkyl, $C_1$–$C_{20}$-acyl;
where $R^1$ and $R^2$, together with the oxygen atoms to which they are bonded and the carbon atoms bonded to the oxygen atoms, can form an unsubstituted or substituted heterocycle;

$R^3$ is hydrogen or a cation selected from the group consisting of alkali metals and alkaline earth metals.

8 Claims, No Drawings

ASCORBYL SORBATES

UV damage to the skin can partly be explained by the action of free radicals. Topically applied ascorbic acid protects the skin from UV damage (D. Darr, Br. J. Dermatol. 127 (1992) 247–253), since ascorbic acid acts against free radicals as an antioxidant.

Experience in the cosmetics industry shows, however, that ascorbic acid is too unstable in most formulations. Therefore derivatives of ascorbic acid are employed which have a higher stability in formulations, but are still able to release ascorbic acid. An example of this is L-ascorbic acid 2-O-D-glucoside which, however, is often not lipophilic enough for use in cosmetics.

Further important free-radical scavengers are tocopherol (vitamin E) and sorbic acid, which are likewise widely employed in the cosmetics sector.

Thus EP-A-O 313 304 describes the use of tocopheryl sorbate as a photoprotector.

Whereas UV filters remain on the skin and thus prevent penetration of the radiation into the skin, tocopheryl sorbate counteracts the formation of free radicals in the skin. Since the active compound is present in the skin, it cannot be rubbed off or washed off and thus offers longer protection than the classical UV filters.

It is the object of the present invention to make available novel free-radical scavengers for cosmetic and pharmaceutical use, which are stable to oxidation and have a wide property profile with respect to their lipophilicity.

We have found that this object is achieved according to the invention by ascorbyl sorbates of the formula I,

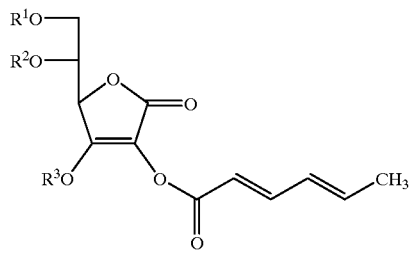

I where the variables independently of one another have the following meanings:

$R^1$ and $R^2$
are hydrogen, $C_1$–$C_{12}$-alkyl, $C_1$–$C_{20}$-acyl;
where $R^1$ and $R^2$, together with the oxygen atoms to which they are bonded and the carbon atoms bonded to the oxygen atoms, can form an unsubstituted or substituted heterocycle;

$R^3$ is hydrogen or a cation selected from the group consisting of $NH_4^+$, alkali metal cations and alkaline earth metal cations.

Preferred compounds of the formula I are those in which the variables independently of one another have the following meanings:

$R^1$ and $R^2$
are hydrogen, $C_6$–$C_{20}$-acyl;

$R^3$ is hydrogen or a cation selected from the group consisting of $NH_4^+$, alkali metal cations and alkaline earth metal cations.

Particularly preferred compounds of the formula I are those in which the variables independently of one another have the following meanings:

$R^1$ and $R^2$
are hydrogen,

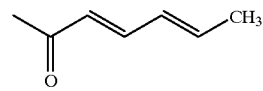

$R^3$ is hydrogen or a cation selected from the group consisting of $NH_4^+$, alkali metal cations and alkaline earth metal cations.

In the case of the ascorbyl sorbates of the formula I according to the invention, acyl radicals for $R^1$ and $R^2$ are understood as meaning branched or unbranched, saturated or unsaturated, if appropriate polyunsaturated, $C_1$–$C_{20}$-acyl chains.

Examples of these are acyl radicals of formic, acetic, propionic, n-butyric, isobutyric, sorbic, n-valeric, isovaleric, caproic, caprylic, capric, undecanoic, lauric, tridecanoic, myristic, pentadecanoic, palmitic, palmitoleic, stearic, oleic, linoleic, linolenic, nonadecanoic and arachidonic acid.

Preferred acyl radicals are those of sorbic acid and those of the long-chain fatty acids having $C_{10}$ to $C_{20}$ carbon atoms, particularly preferably acyl radicals of sorbic, lauric, palmitic, palmitoleic, stearic, oleic and linoleic acid.

Alkyl radicals $R^1$ and $R^2$ which may be mentioned are branched or unbranched $C_1$–$C_{12}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl.

Particularly preferred alkyl radicals are $C_1$–$C_6$-alkyl chains, in particular methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl.

The radicals $R^1$ and $R^2$, together with the oxygen atoms to which they are bonded and the carbon atoms bonded to the oxygen atoms, can form an unsubstituted or substituted heterocycle. Among these are meant, for example, cyclic acetals and ketals, which are employed, inter alia, as protective groups for the two terminal hydroxyl functions (in the 5- and 6-position) of ascorbic acid. A preferred heterocyclic system is, inter alia, the 5,6-iso-propylidene radical, which is formed by reaction of the two free hydroxyl groups in the 5- and 6-position with acetone.

Possible cations $R^3$ are $NH_4^+$ and also representatives from the group consisting of the alkali metals and alkaline earth metals, preferably $NH_4^+$, Na, K, Li, Ca and Mg, particularly preferably Na, K and Mg.

The term ascorbyl sorbates is understood as meaning both sorbic acid derivatives of L- and D-ascorbic acid (isoascorbic acid), preferably of L-ascorbic acid.

An advantage of the ascorbyl sorbates of the formula I is that the stabilizing sorbic acid radical on the ascorbic acid is itself an active group which likewise serves as a free-radical quencher.

Just as with tocopheryl sorbate, good protection from free radicals, such as, for example, are produced by UV radiation, can be achieved with the ascorbyl sorbates of the formula I. Tocopherol, however, can only be linked with one sorbic acid radical. On account of the high molecular weight of tocopherol in contrast to ascorbic acid, linkage of sorbic acid to ascorbic acid is advantageous, as the proportion of active compound per molar weight is higher. In addition, up to four sorbic acid radicals can be linked to the ascorbic acid, which further increases the radical-quenching action. Apart from sorbic acid, other radicals, such as, for example, phosphate, palmitate, can be attached to the ascorbic acid, whereby lipophilicity and solubility of the compound can be affected. The 2-O-sorboyl-L-ascorbic acid according to the invention is water-soluble, 6-O-palmitoyl-2-O-sorboyl-L-ascorbic acid is oil-soluble. It is thus possible to incorporate the ascorbyl sorbates according to the invention in all desired cosmetic formulations. Additionally, owing to the differing lipophilicity of the compounds of the formula I, the penetration into the skin can be controlled. By formulating a mixture of several ascorbyl sorbates of differing lipophilicity, a very wide layer of skin can be protected from UV radiation.

The stable ascorbyl sorbates of the formula I according to the invention are thus outstandingly suitable as active compounds for cosmetic and pharmaceutical preparations.

Thus the compounds are distinguished, inter alia, in that the lipophilicity of the ascorbic acid derivatives can be adjusted in a controlled manner by variation of the radicals $R^1$ and $R^2$. Depending on the requirements in the formulation of cosmetic and pharmaceutical preparations, a wide range of stable vitamin C derivatives are thus available to the expert in the field. The trisorbates and the fatty acid esters of vitamin C 2-monosorbate, particularly, can be incorporated very easily into preparations such as, for example, ointments, lotions, gels or emulsions on account of their good oil solubility.

Accordingly, the present invention also relates to cosmetic and pharmaceutical preparations comprising an effective amount of at least one of the compounds of the formula I, and customary cosmetic and pharmaceutical auxiliaries and additives.

The abovementioned preparations can contain the compounds of the formula I in proportions of from 0.01 to 10% by weight, preferably 0.1 to 8% by weight, particularly preferably 0.5 to 5% 25 by weight, based on the total amount of the cosmetic and pharmaceutical preparation.

The ascorbic acid derivatives of the formula I can be employed, inter alia, in all cosmetic and pharmaceutical preparations which, beside water, also contain emulsifiers, stabilizers, natural oils, cosmetic oils, fats, waxes, silicone oils, silicone oil derivatives, solubilizers, sunscreens, active compounds, moisturizers, consistency-imparting agents, gel-forming agents, antioxidants or preservatives.

Emulsifiers which can be used are, for example, the following substances:

Polyglycerol fatty acid esters, ethoxylates of fatty acids, sorbitan fatty acid esters, phosphoric acid esters of fatty acids, phospholipids, glycerol monostearate and self-emulsifying glycerol monostearate.

Stabilizers are understood as meaning:

Magnesium and aluminum salts of fatty acids, complexing agents such as EDTA, NTA, MGDA, antioxidants such as BHT, BHA, alpha tocopherol, gallic acid and its salts and esters.

Natural oils are, for example, jojoba oil, sunflower oil, ground nut oil, almond oil, avocado oil, macadamia nut oil, castor oil, maizegerm oil, grapeseed oil.

Cosmetic oils are, for example, isopropyl esters of fatty acids, very particularly isopropyl stearate, isopropyl palmitate, isopropyl isostearate, isopropyl myristate, isopropyl laurate, paraffin oil, neutral oil.

Cosmetic active compounds are, for example, panthenol, bisabolol, αtocopherol, α-tocopherol acetate, Aloe vera, algal extract, hyaluronic acid, retinol and retinyl esters, phytantriol, panthenyl ethyl ether, ferulic acid.

Sunscreens which can be used on their own or as a mixture together with the compounds of the formula I are, for example

| No. | Substance | CAS No. (= acid) |
|---|---|---|
| 1 | 4-aminobenzoic acid | 150-13-0 |
| 2 | 3-(4'-trimethylammonium)benzylidenebornan-2-one methylsulfate | 52793-97-2 |
| 3 | 3,3,5-trimethylcyclohexyl salicylate (homosalate) | 118-56-9 |
| 4 | 2-hydroxy-4-methoxybenzophenone (oxybenzone) | 131-57-7 |
| 5 | 2-phenylbenzimidazole-5-sulfonic acid and its potassium, sodium and triethanolamine salts | 27503-81-7 |
| 6 | 3,3'-(1,4-phenylenedimethine)-bis(7,7-dimethyl-2-oxobicyclo[2.2.1]heptane-1-methanesulfonic acid) and its salts | 90457-82-2 |
| 7 | polyethoxyethyl 4-bis(polyethoxy)aminobenzoate | 113010-52-9 |
| 8 | 2-ethylhexyl 4-dimethylaminobenzoate | 21245-02-3 |
| 9 | 2-ethylhexyl salicylate | 118-60-5 |
| 10 | isoamyl 4-methoxycinnamate | 71617-10-2 |
| 11 | 2-ethylhexyl 4-methoxycinnamate | 5466-77-3 |
| 12 | 2-hydroxy-4-methoxybenzophenone-5-sulfonic acid (sulisobenzone) and the sodium salt | 4065-45-6 |
| 13 | 3-(4'-methyl)benzylidenebornan-2-one | 36861-47-9 |
| 14 | 3-benzylidenebornan-2-one | 15087-24-8 |
| 15 | 1-(4'-isopropylphenyl)-3-phenylpropane-1,3-dione | 63250-25-9 |
| 16 | 4-isopropylbenzyl salicylate | 94134-93-7 |
| 17 | 2,4,6-trianiline-(o-carbo-2'-ethyl-hexyl-1'-oxy)-1,3,5-triazine | 88122-99-0 |
| 18 | 3-imidazol-4-yl-acrylic acid and its ethyl | 104-98-3 |

-continued

| No. | Substance | CAS No. (= acid) |
|---|---|---|
| | ester | |
| 19 | ethyl 2-cyano-3,3-diphenylacrylate | 5232-99-5 |
| 20 | 2'-ethylhexyl 2-cyano-3,3-diphenylacrylate | 6197-30-4 |
| 21 | menthyl o-aminobenzoate or: 5-methyl-2-(1-methylethyl) 2-aminobenzoate | 134-09-8 |
| 22 | glyceryl p-aminobenzoate or: 1-glyceryl 4-aminobenzoate | 136-44-7 |
| 23 | 2,2'-dihydroxy-4-methoxybenzophenone (dioxybenzone) | 131-53-3 |
| 24 | 2-hydroxy-4-methoxy-4-methylbenzophenone (mexenone) | 1641-17-4 |
| 25 | triethanolamine salicylate | 2174-16-5 |
| 26 | dimethoxyphenylglyoxalic acid or: sodium 3,4-dimethoxyphenylglyoxalate | 4732-70-1 |
| 27 | 3-(4'-sulfo)benzylidenebornan-2-one and its salts | 56039-58-8 |
| 28 | 4-tert-butyl-4'-methoxydibenzoylmethane | 70356-09-1 |
| 29 | 2,2',4,4'-tetrahydroxybenzophenone | 131-55-5 |

The ascorbyl sorbates of the formula I are also suitable for surfactant formulations.

Thus hair rinses, shampoos and foams with stable vitamin C of the formula I can be prepared without problems.

The combination of anionic surfactants with cationic surfactants does not restrict the use in cosmetic products.

The ascorbyl sorbates of the formula I are synthesized in a manner known per se by base-catalyzed reaction of the ascorbic acid derivatives of formula II

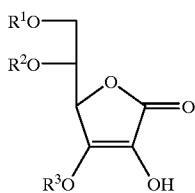

II wherein groups $R^1$, $R^2$ and $R^3$ are as defined above, with sorbic acid or a sorbic acid derivative, preferably sorbyl chloride. In particular, as disclosed by B. M. Tolberg et al, Ann., N.Y. Acad. Sci., 258 (1975) 48–69, ascorbic acid is reacted with a base such as an alkali metal hydroxide in aqueous solution to give ascorbate salt compound, which is reacted with an acyl halide. (See, in particular, page 48, second paragraph, and the paragraph bridging pages 48 and 49, as well as particularly the reaction scheme on page 49 (top) and the acyl derivatized (position-3) ascorbic acid compounds shown in Table 1).

In the following examples, the preparation of the ascorbic acid derivatives of the formula I according to the invention and cosmetic formulations comprising these compounds is illustrated in greater detail.

EXAMPLE 1

2,5,6-O-trisorboyl-L-ascorbic Acid 2 g (11.36 mmol; 1 eq.) of L-ascorbic acid were suspended with 50 ml of dichloromethane in a 100 ml 3-necked flask. In succession, 0.28 g (2.27 mmol; 0.2 eq.) of N,N'-dimethyl-aminopyridine, 5.2 ml (37.49 mmol; 3.3 eq.) of triethylamine and finally, slowly, 4.89 g (37.49 mmol; 3.3 eq.) of sorboyl chloride were added dropwise at −15° C. The mixture was then stirred overnight at 0°C. The salt which was deposited was filtered off and the filtrate was extracted with 1 M HCl. The organic phase was extracted with saturated NaCl solution, dried over $MgSO_4$ and then concentrated.

Yield: 4.4 g (85% yield)

EXAMPLE 2

5,6-O-Isopropylidene-2-O-sorboyl-L-ascorbic Acid 100.0 g (462.5 mmol; 1 eq.) of 5,6-O-isopropylidene-L-ascorbic acid were dissolved in 900 ml of dichloromethane in an $N_2$ atmosphere in a 2 l 4-necked flask. In succession, 11.30 g (92.51 nmol; 0.2 eq.) of dimethylaminopyridine and 64.0 ml (462.5 mmol; 1 eq.) of triethylamine were added. 60.37 g (462.5 mmol; 1 eq.) of sorboyl chloride, dissolved in 100 ml of dichloromethane, were then slowly added dropwise at −15° C., the internal temperature not exceeding −10° C. The mixture was then stirred at room temperature for 10 hours, and washed with 0.1 M HCl and then $H_2O$. An extraction was then carried out with saturated aqueous sodium hydrogencarbonate solution. The organic phase was separated off and the aqueous phase was treated with concentrated hydrochloric acid to pH 1. In this process, a white precipitate was deposited, which was dried in an oil pump vacuum.

Yield: 83 g (58% yield)

EXAMPLE 3

2-O-Sorboyl-L-ascorbic Acid 5 g (0.012 mol) of 5,6-O-isopropylidene-2-O-sorboyl-L-ascorbic acid were dissolved in 160 ml of acetic acid (60%) in a 250 ml 2-necked flask and the solution was stirred at 50° C. for 4 hours, then concentrated on a rotary evaporator and codistilled with toluene. The crude product was purified on silica gel (eluent dichloromethane/methanol 5:1).

Yield: 3.1 g (96% yield)

EXAMPLE 4

6-O-Palmitoyl-2-O-sorboyl-L-ascorbic Acid 50 g (120 mmol; 1 eq.) of 6-O-palmitoyl-L-ascorbic acid were dissolved in 400 ml of pyridine in a 1 l 4-necked flask. 23.40 g (130 mmol; 1.1 eq.) of sorboyl chloride, dissolved in 30 ml of dichloromethane, were slowly added dropwise at an internal temperature of −15° C. Care was taken here that the internal temperature did not exceed −10° C. The mixture was brought to room temperature and additionally stirred for 2 hours. The reaction solution was concentrated on a rotary evaporator and then codistilled with toluene. The residue was taken up in a little dichloromethane and extracted with 1 M HCl. The organic phase was concentrated somewhat and treated with an excess of n-hexane. A white precipitate was deposited, which was dried in an oil pump vacuum.

Yield: 28 g (46% yield)

Cosmetic Preparations

EXAMPLE 5
Composition for Fat-Free Sunscreen Gel
Mass content (% by weight)

| | |
|---|---|
| 0.40 | acrylate/$C_{10}$–$C_{30}$ alkylacrylate crosspolymer |
| 0.25 | hydroxyethylcellulose |
| 8.00 | octyl methoxycinnamate |
| 1.00 | 4-methylbenzylidenecamphor |
| 0.50 | 6-O-palmitoyl-2-O-sorboyl-L-ascorbic acid |
| 0.20 | disodium EDTA |
| 5.00 | glycerol |
| 0.15 | fragrance |
| 0.30 | imidazolidinylurea |
| 0.25 | sodium methylparaben |
| 0.15 | sodium propylparaben |
| 5.00 | PEG-25 PABA |
| 0.10 | sodium hydroxide |
| to 100 | water |

EXAMPLE 6
Composition for Moisturizing Cream
Mass content (% by weight)

| | |
|---|---|
| 6.00 | PEG-7-hydrogenated castor oil |
| 5.00 | isopropyl palmitate |
| 6.00 | mineral oil |
| 5.00 | jojoba oil |
| 5.00 | almond oil |
| 0.50 | tocopheryl acetate |
| 2.00 | 2,5,6-O-trisorboyl-L-ascorbic acid |
| 0.60 | magnesium stearate |
| 2.00 | PEG-45/dodecyl glycol copolymer |
| 5.00 | glycerol |
| 0.25 | methylparaben |
| 0.15 | propylparaben |
| 5.00 | imidazolidinylurea |
| 0.15 | fragrance |
| 0.20 | disodium EDTA |
| to 100 | water |

EXAMPLE 7
Composition for Moisturizing Cream
Mass content (% by weight)

| | |
|---|---|
| 6.00 | PEG-7-hydrogenated castor oil |
| 5.00 | isopropyl palmitate |
| 6.00 | mineral oil |
| 5.00 | jojoba oil |
| 5.00 | almond oil |
| 0.50 | tocopheryl acetate |
| 2.00 | 6-O-palmitoyl-2-O-sorboyl-L-ascorbic acid |
| 0.60 | magnesium stearate |
| 2.00 | PEG-45/dodecyl glycol copolymer |
| 5.00 | glycerol |
| 0.25 | methylparaben |
| 0.15 | propylparaben |
| 5.00 | imidazolidinylurea |

-continued

| | |
|---|---|
| 0.15 | fragrance |
| 0.20 | disodium EDTA |
| to 100 | water |

EXAMPLE 8
Composition for Night Cream without Preservative
Mass content (% by weight)

| | |
|---|---|
| 5.00 | PEG-7-hydrogenated castor oil |
| 4.00 | isopropyl palmitate |
| 4.00 | caprylic acid/caproate triglyceride |
| 3.00 | 6-O-palmitoyl-2-O-sorboyl-L-ascorbic acid |
| 1.50 | PEG-45/dodecyl glycol copolymer |
| 0.50 | magnesium stearate |
| 1.50 | dimethicone |
| 4.00 | 1,2-propylene glycol |
| 4.00 | glycerol |
| 8.00 | 611 alcohol |
| 2.00 | collagen |
| 0.15 | fragrance |
| to 100 | water |

EXAMPLE 9
Composition for Antiwrinkle Cream
Mass content (% by weight)

| | |
|---|---|
| 6.00 | PEG-7-hydrogenated castor oil |
| 5.00 | isopropyl palmitate |
| 10.00 | mineral oil |
| 3.00 | caprylic acid/caprate triglyceride |
| 0.60 | magnesium stearate |
| 1.00 | 2-O-sorboyl-L-ascorbic acid |
| 1.50 | tocopheryl acetate |
| 2.00 | PEG-45/dodecyl glycol copolymer |
| 0.05 | tocopherol |
| 0.20 | retinol |
| 0.30 | glycerol |
| 0.70 | magnesium sulfate |
| 0.25 | methylparaben |
| 0.15 | propylparaben |
| 0.20 | sodium ascorbyl monophosphate |
| 0.10 | α-tocopherol |
| 0.10 | ascorbyl palmitate |
| 0.15 | fragrance |
| to 100 | water |

EXAMPLE 10
Composition for Antiwrinkle Cream
Mass content (% by weight)

| | |
|---|---|
| 6.00 | PEG-7-hydrogenated castor oil |
| 5.00 | isopropyl palmitate |
| 10.00 | mineral oil |
| 3.00 | caprylic acid/caprate triglyceride |
| 0.60 | magnesium stearate |
| 1.00 | 5,6-O-isopropylidene-2-O-sorboyl-L-ascorbic acid |
| 1.50 | tocopheryl acetate |
| 2.00 | PEG-45/dodecyl glycol copolymer |
| 0.05 | tocopherol |
| 0.20 | retinol |
| 0.30 | glycerol |
| 0.70 | magnesium sulfate |
| 0.25 | methylparaben |

-continued

| | |
|---|---|
| 0.15 | propylparaben |
| 0.20 | sodium ascorbyl monophosphate |
| 0.10 | α-tocopherol |
| 0.10 | ascorbyl palmitate |
| 0.15 | fragrance |
| to 100 | water |

EXAMPLE 11
Composition for Moisturizing Day Cream
Mass content (% by weight)

| | |
|---|---|
| 2.00 | ceteareth/6 |
| 2.00 | ceteareth/25 |
| 10.00 | mineral oil |
| 3.00 | caprylic acid/caprate triglyceride |
| 3.00 | isostearic acid |
| 3.00 | 6-O-palmitoyl-2-O-sorboyl-L-ascorbic acid |
| 1.50 | tocopheryl acetate |
| 2.00 | D-panthenol USP |
| 0.05 | tocopherol |
| 0.20 | retinol |
| 0.30 | glycerol |
| 0.15 | dibromocyanobutane |
| 0.20 | sodium ascorbyl monophosphate |
| 0.10 | α-tocopherol |
| 0.10 | ascorbyl palmitate |
| 0.15 | fragrance |
| to 100 | water |

EXAMPLE 12
Composition for Moisturizing Day Cream
Mass content (% by weight)

| | |
|---|---|
| 2.00 | ceteareth/6 |
| 2.00 | ceteareth/25 |
| 10.00 | mineral oil |
| 3.00 | caprylic acid/caprate triglyceride |
| 3.00 | isostearic acid |
| 3.00 | 2-O-sorboyl-L-ascorbic acid |
| 1.50 | tocopheryl acetate |
| 2.00 | D-panthenol USP |
| 0.05 | tocopherol |
| 0.20 | retinol |
| 0.30 | glycerol |
| 0.15 | dibromocyanobutane |
| 0.20 | sodium ascorbyl monophosphate |
| 0.10 | α-tocopherol |
| 0.10 | ascorbyl palmitate |
| 0.15 | fragrance |
| to 100 | water |

EXAMPLE 13
Composition for Fat-Free Gel
Mass content (% by weight)

| | |
|---|---|
| 8.00 | octyl methoxycinnamate |
| 7.00 | titanium dioxide |
| 2.00 | 2-O-sorboyl-L-ascorbic acid |
| 5.00 | glycerol |
| 5.00 | PEG-25 PABA |
| 1.00 | 4-methylbenzylidenecamphor |
| 0.40 | acrylates/C10–C30-alkyl acrylate crosspolymer |
| 0.30 | imidazolidinylurea |

-continued

| | |
|---|---|
| 0.25 | hydroxyethylcellulose |
| 0.25 | sodium methylparaben |
| 0.20 | disodium EDTA |
| 0.15 | fragrance |
| 0.15 | sodium propylparaben |
| 0.10 | sodium hydroxide |
| to 100 | water |

EXAMPLE 14
Composition for Suncream (SPF 20)
Mass content (% by weight)

| | |
|---|---|
| 8.00 | octyl methoxycinnamate |
| 8.00 | titanium dioxide |
| 6.00 | PEG-7-hydrogenated castor oil |
| 2.00 | 2-O-sorboyl-L-ascorbic acid |
| 6.00 | mineral oil |
| 5.00 | zinc oxide |
| 5.00 | isopropyl palmitate |
| 5.00 | imidazolidinylurea |
| 3.00 | jojoba oil |
| 2.00 | PEG-45/dodecyl glycol copolymer |
| 1.00 | 4-methylbenzylidenecamphor |
| 0.60 | magnesium stearate |
| 0.50 | tocopheryl acetate |
| 0.25 | methylparaben |
| 0.20 | disodium EDTA |
| 0.15 | propylparaben |
| to 100 | water |

EXAMPLE 15
Composition for Suncream (water-resistant)
Mass content (% weight)

| | |
|---|---|
| 8.00 | octyl methoxycinnamate |
| 5.00 | PEG-7-hydrogenated castor oil |
| 5.00 | propylene glycol |
| 4.00 | isopropyl palmitate |
| 4.00 | caprylic/capric triglyceride |
| 3.00 | 6-O-palmitoyl-2-O-sorboyl-L-ascorbic acid |
| 4.00 | glycerol |
| 3.00 | jojoba oil |
| 2.00 | 4-methylbenzylidenecamphor |
| 2.00 | titanium dioxide |
| 1.50 | PEG-45/dodecyl glycol copolymer |
| 1.50 | dimethicone |
| 0.70 | magnesium sulfate |
| 0.50 | magnesium stearate |
| 0.15 | fragrance |
| to 100 | water |

EXAMPLE 16
Composition for Sun Milk (SPF 6)
Mass content (% by weight)

| | |
|---|---|
| 10.00 | mineral oil |
| 6.00 | PEG-7-hydrogenated castor oil |
| 5.00 | isopropyl palmitate |
| 3.50 | octyl methoxycinnamate |
| 2.00 | 2,5,6-trisorboyl-L-ascorbic acid |
| 3.00 | caprylic/capric triglyceride |
| 3.00 | jojoba oil |
| 2.00 | PEG-45/dodecyl glycol copolymer |

-continued

| | |
|---|---|
| 0.70 | magnesium sulfate |
| 0.60 | magnesium stearate |
| 0.50 | tocopheryl acetate |
| 0.30 | glycerol |
| 0.25 | methylparaben |
| 0.15 | propylparaben |
| 0.05 | tocopherol |
| to 100 | water |

EXAMPLE 17

Composition for Lipstick
Mass content (% by weight)

| | |
|---|---|
| 10.00 | glycerol |
| 10.00 | titanium dioxide |
| 2.00 | 2,5,6-trisorboyl-L-ascorbic acid |
| 8.00 | octyl methoxycinnamate |
| 5.00 | zinc oxide |
| 4.00 | castor oil |
| 4.00 | pentaerythrithyl stearate/caprate/caprylate adipate |
| 3.00 | glyceryl stearate SE |
| 2.00 | beeswax |
| 2.00 | microcrystalline wax |
| 2.00 | quaternium-18 bentonite |
| 1.50 | PEG-45/dodecyl glycol copolymer |
| to 100 | Eucerinum anhydricum |

EXAMPLE 18

Composition for Sunblock with Micropigments
Mass content (% by weight)

| | |
|---|---|
| 10.00 | parsol MCX octyl methoxycinnamate |
| 6.00 | PEG-7-hydrogenated castor oil |
| 6.00 | titanium dioxide |
| 2.00 | 5,6-O-isopropylidene-2-O-sorboyl-L-ascorbic acid |
| 5.00 | mineral oil |
| 5.00 | isoamyl p-methoxycinnamate |
| 5.00 | propylene glycol |
| 3.00 | jojoba oil |
| 3.00 | 4-methylbenzylidenecamphor |
| 2.00 | PEG-45/dodecyl glycol copolymer |
| 1.00 | butyl methoxydibenzoylmethane |
| 1.00 | dimethicone |
| 0.50 | PEG-40-hydrogenated castor oil |
| 0.50 | tocopheryl acetate |
| 0.50 | phenoxyethanol |
| 0.20 | EDTA |
| to 100 | water |

We claim:

1. An ascorbyl sorbate of the formula I,

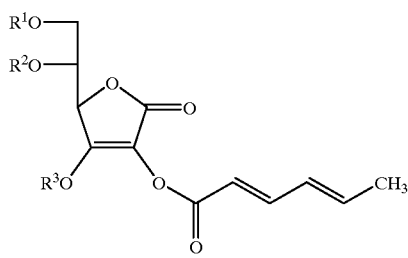

where the variables independently of one another have the following meanings:

$R^1$ and $R^2$
are each hydrogen, $C_1$–$C_{12}$-alkyl, or $C_1$–$C_{20}$-acyl;
where $R^1$ and $R^2$, together with the oxygen atoms to which they are bonded and the carbon atoms bonded to the oxygen atoms, can form an unsubstituted or substituted heterocycle;

$R^3$ is hydrogen or a cation selected from the group consisting of $NH_4^+$, alkali metal cations and alkaline earth metal cations.

2. An ascorbyl sorbate of the formula I as claimed in claim 1, where the variables independently of each another have the following meanings:

$R^1$ and $R^2$
are hydrogen, or $C_6$–$C_{20}$-acyl;

$R^3$ is hydrogen or a cation selected from the group consisting of $NH_4^+$, alkali metal cations and alkaline earth metal cations.

3. The ascorbyl sorbate of the formula I as claimed in claim 1, where the variables independently of each another have the following meanings:

$R^1$ and $R^2$
are hydrogen,

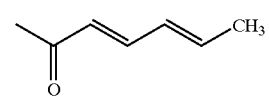

$R^3$ is hydrogen or a cation selected from the group consisting of $NH_4^+$, alkali metal cations and alkaline earth metal cations.

4. A process for preparing an ascorbyl sorbate of the formula I as claimed in claim 1, which comprises reacting ascorbic acid or ascorbic acid derivatives of the formula II, where the substituents $R^1$ to $R^3$ have the meanings mentioned in claim 1, with sorbic acid or a sorbic acid derivative,

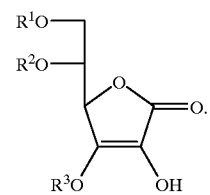

5. The process as claimed in claim 4, wherein ascorbic acid or ascorbic acid derivative of the formula II each reacted with sorboyl chloride.

6. A cosmetic or pharmaceutical preparation comprising an effective amount of at least one compound of formula I as claimed in claim 1, and customary cosmetic and pharmaceutical auxiliaries and additives.

7. A method of preparing cosmetic and pharmaceutical preparations, comprising:
incorporating the ascorbyl sorbate of claim 1 into the other ingredients and additives of a cosmetic or pharmaceutical preparation.

8. The method of claim 7, wherein said ascorbyl sorbate functions as an antioxidant in the cosmetic or pharmaceutical preparation.

* * * * *